US007351235B2

(12) United States Patent
Chiou

(10) Patent No.: US 7,351,235 B2
(45) Date of Patent: Apr. 1, 2008

(54) SNIVEL REMOVING DEVICE

(76) Inventor: Jackey Chiou, No. 124, Chengong 3rd Road, Nangan Gonyeh Chu, Nantou 54066 (TW)

( * ) Notice: Subject to any disclaimer, the term of this patent is extended or adjusted under 35 U.S.C. 154(b) by 448 days.

(21) Appl. No.: 11/086,645

(22) Filed: Mar. 22, 2005

(65) Prior Publication Data

US 2006/0241565 A1  Oct. 26, 2006

(51) Int. Cl.
  *A61M 27/00* (2006.01)
(52) U.S. Cl. .................. 604/319; 604/73; 604/315
(58) Field of Classification Search ............ 604/73, 604/236, 315, 319, 540
  See application file for complete search history.

(56) References Cited

U.S. PATENT DOCUMENTS

| | | | | |
|---|---|---|---|---|
| 350,895 | A * | 10/1886 | Rualt ........................... | 604/30 |
| 2,078,180 | A * | 4/1937 | Kronenberg .................. | 604/28 |
| 2,501,567 | A * | 3/1950 | Huck ........................... | 411/39 |
| 2,597,344 | A * | 5/1952 | Lang ........................... | 411/449 |
| 2,815,715 | A * | 12/1957 | Tremblay .................... | 417/244 |
| 3,542,026 | A * | 11/1970 | Bledsoe ....................... | 604/185 |
| 3,892,226 | A * | 7/1975 | Rosen .......................... | 600/563 |
| 3,946,735 | A * | 3/1976 | DeWall ........................ | 604/133 |
| 4,136,696 | A * | 1/1979 | Nehring ........................ | 604/142 |
| 4,344,743 | A * | 8/1982 | Bessman et al. ............. | 417/317 |
| 4,384,829 | A * | 5/1983 | Conley et al. ............... | 417/412 |
| 4,403,611 | A * | 9/1983 | Babbitt et al. ................ | 604/73 |
| 4,749,337 | A * | 6/1988 | Dickinson et al. ........ | 417/199.1 |
| 4,799,924 | A * | 1/1989 | Rosenblatt ................... | 604/181 |
| 4,981,474 | A * | 1/1991 | Bopp et al. .................. | 604/133 |
| 4,995,386 | A * | 2/1991 | Ng ........................ | 128/205.19 |
| 5,024,653 | A * | 6/1991 | Kohnke ........................ | 604/35 |
| 5,062,835 | A * | 11/1991 | Maitz et al. ................. | 604/153 |
| 5,167,621 | A * | 12/1992 | Band et al. ................... | 604/35 |
| 5,209,654 | A * | 5/1993 | Lofsjogard Nilsson et al. .. | 417/478 |
| 5,318,548 | A * | 6/1994 | Filshie ........................ | 604/319 |
| 5,342,329 | A * | 8/1994 | Croquevielle ............... | 604/319 |
| 5,713,728 | A * | 2/1998 | Salamey ...................... | 417/418 |
| 5,928,190 | A * | 7/1999 | Davis ....................... | 604/94.01 |
| 6,135,980 | A * | 10/2000 | Vu ............................... | 604/73 |
| 6,290,667 | B1 * | 9/2001 | Cook ........................... | 604/19 |
| 6,328,718 | B1 * | 12/2001 | Chiang et al. .............. | 604/319 |
| 6,382,928 | B1 * | 5/2002 | Chang ......................... | 417/269 |
| 6,471,679 | B1 * | 10/2002 | Suh ............................. | 604/319 |
| 6,517,511 | B2 * | 2/2003 | Yao .............................. | 604/35 |
| 6,595,949 | B1 * | 7/2003 | Shapiro ....................... | 604/73 |
| 6,607,368 | B1 * | 8/2003 | Ross et al. ................... | 417/412 |

(Continued)

FOREIGN PATENT DOCUMENTS

WO  WO88/10124  * 12/1988

*Primary Examiner*—Tatyana Zalukaeva
*Assistant Examiner*—Paula L. Craig
(74) *Attorney, Agent, or Firm*—Charles E. Baxley

(57) ABSTRACT

A snivel removing device includes a housing having a partition to form two chambers and an outlet port and an inlet port communicating with the chambers. One or more bladders are attached to the housing, and communicating with the chambers, and compressible and expandable to draw the snivel into one of the chambers of the housing via the inlet port, and then into the other chamber of the housing, and to flow out through the outlet port of the housing. Two or more check valve may be used to control the flowing of the snivel. An arm is attached to each bladder, and an operating device may operate the arm to depress and to expand the bladder.

15 Claims, 6 Drawing Sheets

U.S. PATENT DOCUMENTS

| | | |
|---|---|---|
| 7,011,621 B2* | 3/2006 | Sayet et al. .................... 600/30 |
| 2002/0081207 A1* | 6/2002 | Ross et al. .................... 417/53 |
| 2003/0109854 A1* | 6/2003 | Chen .......................... 604/540 |
| 2004/0087866 A1* | 5/2004 | Bowman et al. ............. 600/529 |
| 2005/0103340 A1* | 5/2005 | Wondka ................. 128/204.18 |
| 2007/0217929 A1* | 9/2007 | Chiou ......................... 417/412 |

* cited by examiner

SNIVEL REMOVING DEVICE

BACKGROUND OF THE INVENTION

1. Field of the Invention

The present invention relates to a snivel removing device, and more particularly to a snivel removing device for easily vacuuming or drawing and cleaning or removing snivel or nasal mucus from users or patients.

2. Description of the Prior Art

Typical snivel removing devices comprise a bladder having a nozzle formed or provided on one end thereof, for engaging into a nose of a user, and for vacuuming and cleaning or removing snivel or nasal mucus from the user or the patients.

In operation, the users have to squeeze the bladder in reciprocating action or frequently, in order to vacuum or to draw the snivel or nasal mucus out of the nose of the user. However, for most of the patients, they may have no enough power or strength to squeeze the bladder, and thus may not suitably operate the typical snivel removing devices.

The present invention has arisen to mitigate and/or obviate the afore-described disadvantages of the conventional snivel removing devices.

SUMMARY OF THE INVENTION

The primary objective of the present invention is to provide a snivel removing device for being actuated or operated by electric actuating device, and for easily vacuuming or drawing and cleaning or removing snivel or nasal mucus from the users or patients.

In accordance with one aspect of the invention, there is provided a snivel removing device comprising a housing including a partition provided therein, to separate an inner portion of the housing into a first chamber and a second chamber, the housing including at least one outlet port provided thereon and communicating with the first chamber thereof, and including an inlet port provided thereon and communicating with the second chamber thereof, for coupling to a nose of a user, to receive the snivel from the user, at least one bladder attached to the housing, and communicating with the first chamber and the second chamber of the housing, and an actuating device for actuating the bladder to draw the snivel into the second chamber of the housing via the inlet port, and then into the first chamber of the housing, and to flow out through the outlet port of the housing.

The housing includes a first check valve attached thereto and disposed between the bladder and the first chamber of the housing, and arranged to allow the snivel to flow from the bladder into the first chamber of the housing only, and to prevent the snivel from flowing backward from the first chamber of the housing into the bladder, and includes a second check valve attached thereto and disposed between the bladder and the second chamber of the housing, and arranged to allow the snivel to flow from the second chamber of the housing into the bladder only, and to prevent the snivel from flowing backward from the bladder into the second chamber of the housing.

The housing includes a first cavity and a second cavity formed therein and communicating with the first and the second chambers of the housing respectively, the first and the second check valves each includes a shank extended therefrom, for engaging through the housing, and each includes a ratchet catch provided on the shank for engaging with the housing, to anchor and secure the first and the second check valves to the housing, and each includes a blade provided on the shank for engaging with the housing, and for selectively blocking the first and the second cavities of the housing respectively.

The shanks of the first and the second check valves each includes a free end portion cut off after the ratchet catches have been engaged through and engaged with the housing. The housing includes two annular depressions formed therein and communicating with the first and the second cavities of the housing respectively, to form two peripheral bulges which are located around the first and the second cavities of the housing respectively, and provided for engaging with the blades of the first and the second check valves respectively.

The actuating device includes an arm attached to the bladder, and an operating device for operating the arm to depress and to expand the bladder, in order to draw the snivel form the inlet port of the housing toward the outlet port of the housing. The operating device includes a magnetic member attached to the arm, and an electro-magnetic device to actuate the magnetic member to operate the arm. The housing includes a retainer provided thereon, and the arm includes a first end pivotally coupled to the retainer of the housing, and a second end having the magnetic member attached thereto.

A container may further be provided and may include at least one entrance provided therein, for engaging with the outlet port of the housing, and for receiving the snivel from the first chamber of the housing. The container includes a partition disposed therein, to separate an inner portion of the container into a first space and a second space, the first space is coupled to the inlet port of the housing, and the second space is communicating with the entrance of the container, to receive the snivel from the first chamber of the housing. The container includes a nozzle coupled to the first space of the container, for engaging into the nose of the user, to receive the snivel from the user.

An outer receptacle may further be provided and may include an opening formed therein, the container is engaged in the opening of the outer receptacle, and includes a peripheral groove formed therein, for engaging with the outer receptacle, and for anchoring the container to the outer receptacle. A platform may further be provided and disposed in the outer receptacle, to support the housing in the outer receptacle.

The outer receptacle includes a number of studs disposed therein and engaged with the platform, to support the platform within the outer receptacle. The studs each includes an enlarged head for engaging with the outer receptacle, and a ratchet catch for engaging with the platform, to anchor the platform within the outer receptacle. The studs each includes a pin extended from the ratchet catch thereof, for allowing the ratchet catch to be easily engaged through the platform, and the pin is cut off from the stud after the ratchet catch has been engaged through the platform to secure the platform within the outer receptacle.

The platform includes a pathway formed therein and aligned with the outlet port of the housing, and includes a passage formed therein and aligned with the inlet port of the housing. The platform includes a fence extended therein, to separate an inner portion of the platform into two separated compartments.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
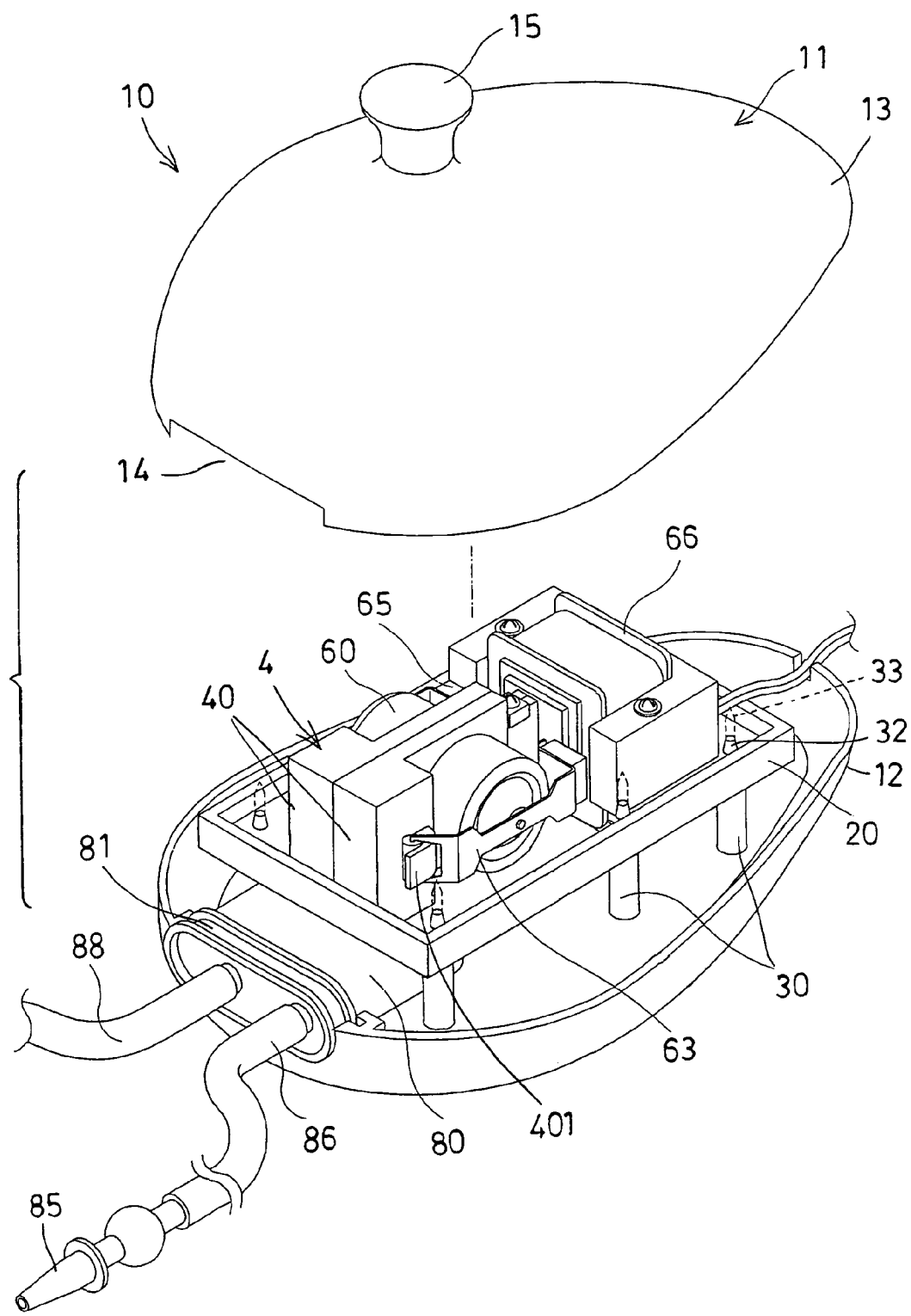
FIG. 1 is a partial exploded view of a snivel removing device in accordance with the present invention.
Figure 2:
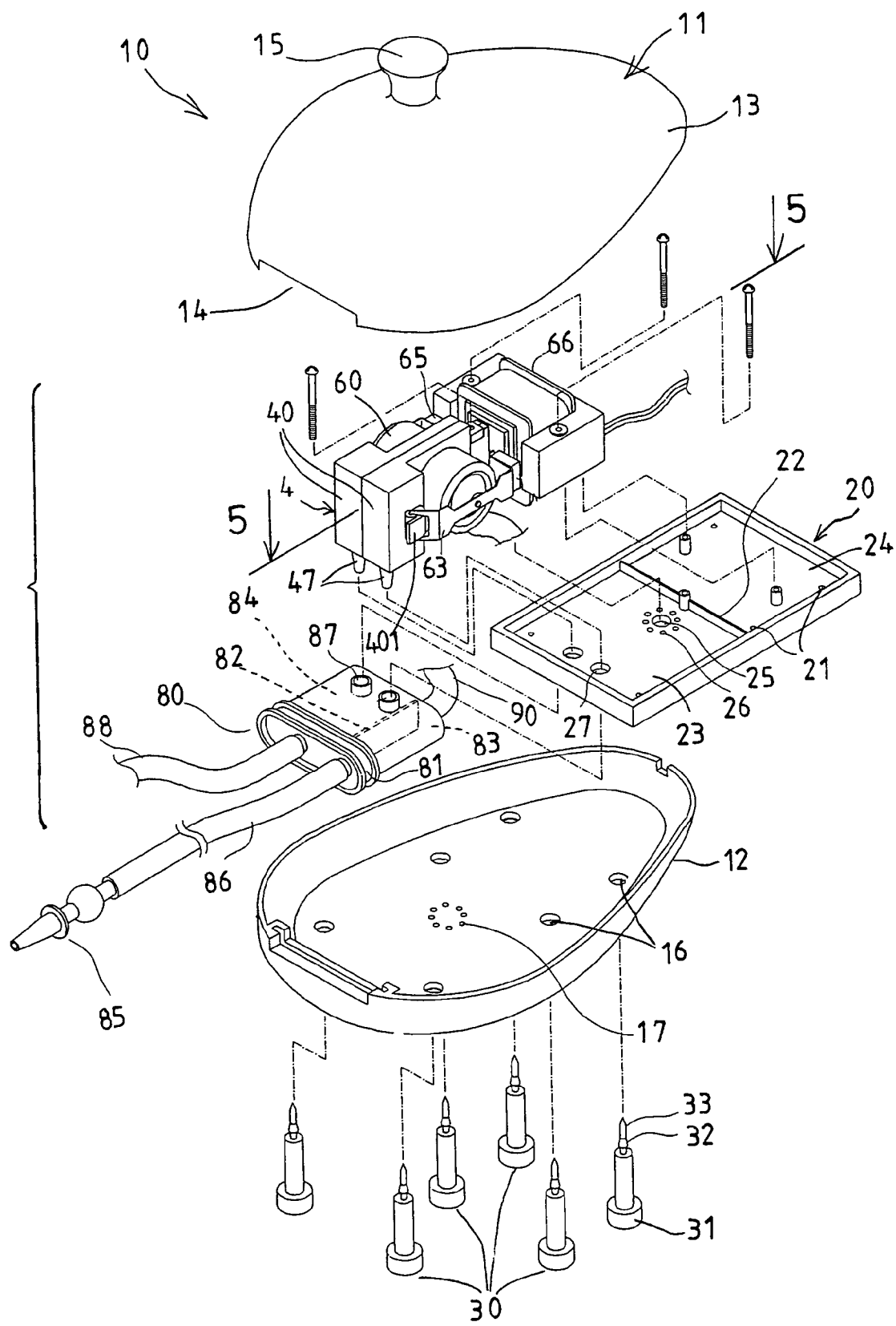
FIG. 2 is another partial exploded view of the snivel removing device.
Figure 3:
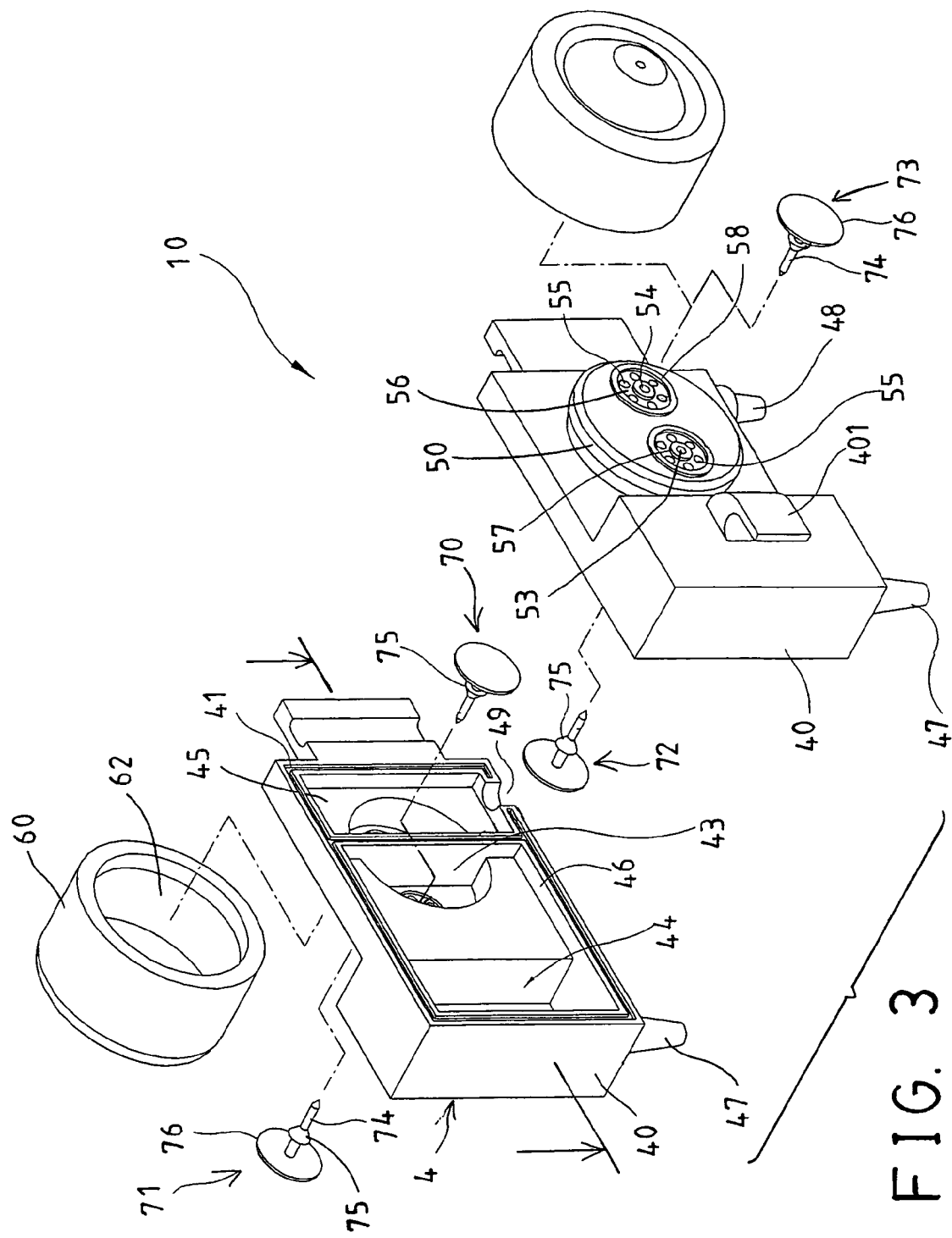
FIG. 3 is a further partial exploded view of the snivel removing device.

Referring to the drawings, and initially to FIGS. 1 and 2, a snivel removing device 10 in accordance with the present invention comprises an outer receptacle 11 including such as two members 12, 13 or a base member 12 and an upper member 13 to be secured together with fasteners (not shown), or by welding processes, and including an opening 14 formed or provided in a front portion thereof.

It is preferable that the outer receptacle 11 includes a handgrip or knob 15 formed or provided on top thereof, for holding or carrying or operating the snivel removing device 10. The base member 12 of the outer receptacle 11 includes a number of holes 16 formed therein and preferably arranged around the outer peripheral portion thereof, and further includes a number of air perforations 17 formed therein for air circulation purposes.

A platform 20 is disposed in the outer receptacle 11, and includes a number of orifices 21 formed therein and aligned with the holes 16 of the outer receptacle 11, for engaging with studs 30 which may be used to support and to cushion the platform 20 within the outer receptacle 11. For example, each of the studs 30 includes an enlarged head 31 for engaging with the base member 12 of the outer receptacle 11, and a ratchet catch 32 for engaging through the orifices 21 of the platform 20, for securing the platform 20 within the outer receptacle 11.

It is preferable that each of the studs 30 further includes a needle member or a pin 33 extended from the ratchet catch 32 thereof, for allowing the ratchet catch 32 to be easily engaged through the orifices 21 of the platform 20 and to be easily engaged with the platform 20. After the ratchet catch 32 has been engaged through the orifices 21 of the platform 20 to secure the platform 20 within the outer receptacle 11, the pin 33 may be cut off from the stud 30, as shown in dotted lines in FIG. 1. The studs 30 may be made of rubber or soft or other materials for cushioning the platform 20.

The platform 20 preferably further includes a fence 22 extended therein, to separate the inner portion of the platform 20 into two separated compartments 23, 24, and includes a passage 25 formed therein, and includes a number of perforations 26 formed therein and preferably arranged around the passage 25 thereof, and aligned with the air perforations 17 of the base member 12 of the outer receptacle 11. The platform 20 further includes one or more, such as two pathways 27 formed therein and communicating with one of the compartments 23 thereof.

Figure 4:
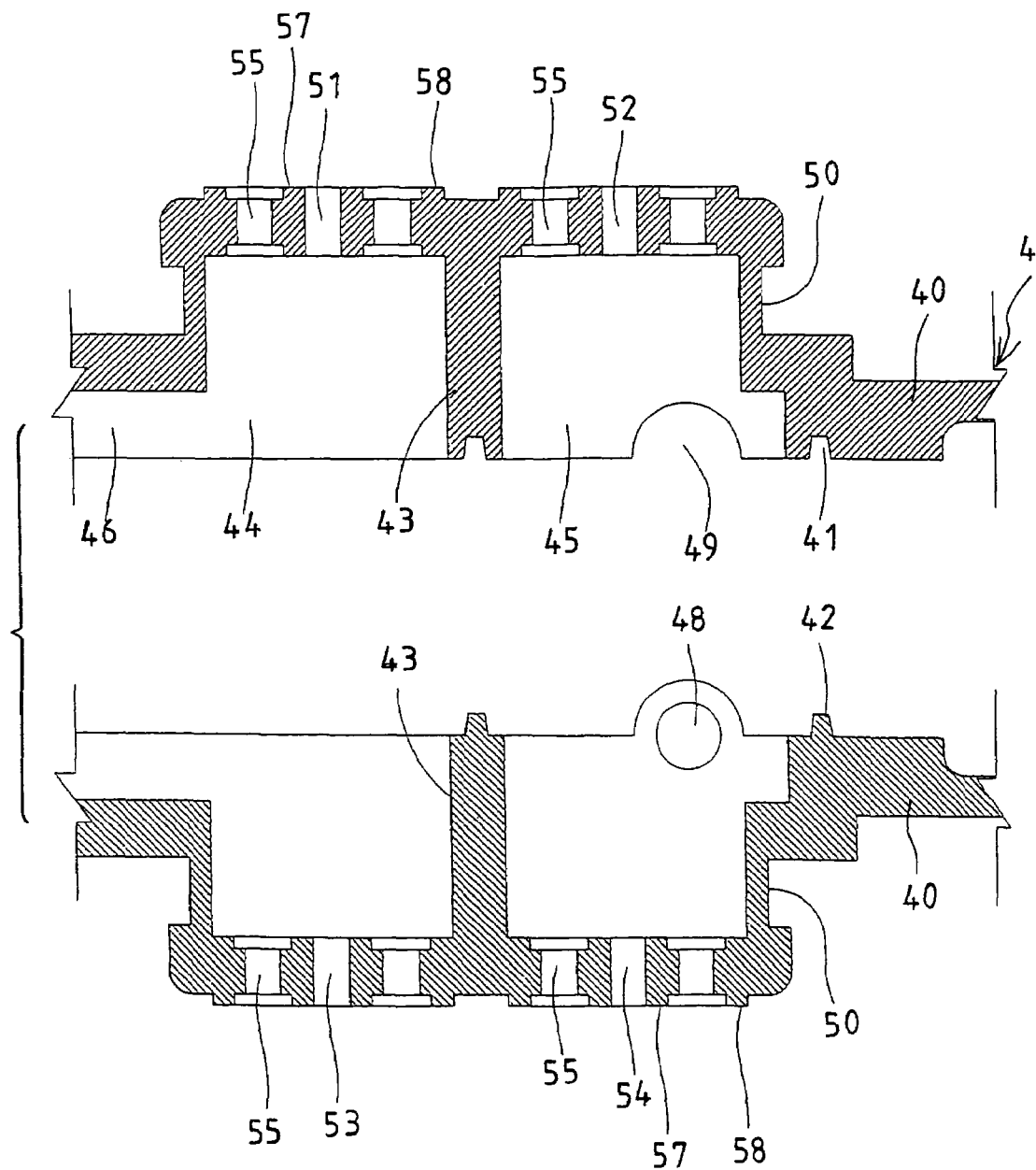
FIG. 4 is a partial cross sectional view of the snivel removing device, taken along lines 4-4 of FIG. 3.

A housing 4 includes two housing members 40 to be anchored or secured together. For example, one of the housing members 40 includes a peripheral recess 41 formed therein, and the other housing member 40 includes a peripheral protrusion 42 extended therefrom (FIG. 4), for engaging into the peripheral recess 41 of the other housing member 40, and thus for anchoring or securing the two housing members 40 together. The two housing members 40 may further be solidly secured together with fasteners (not shown), or by welding processes.

Figure 5:
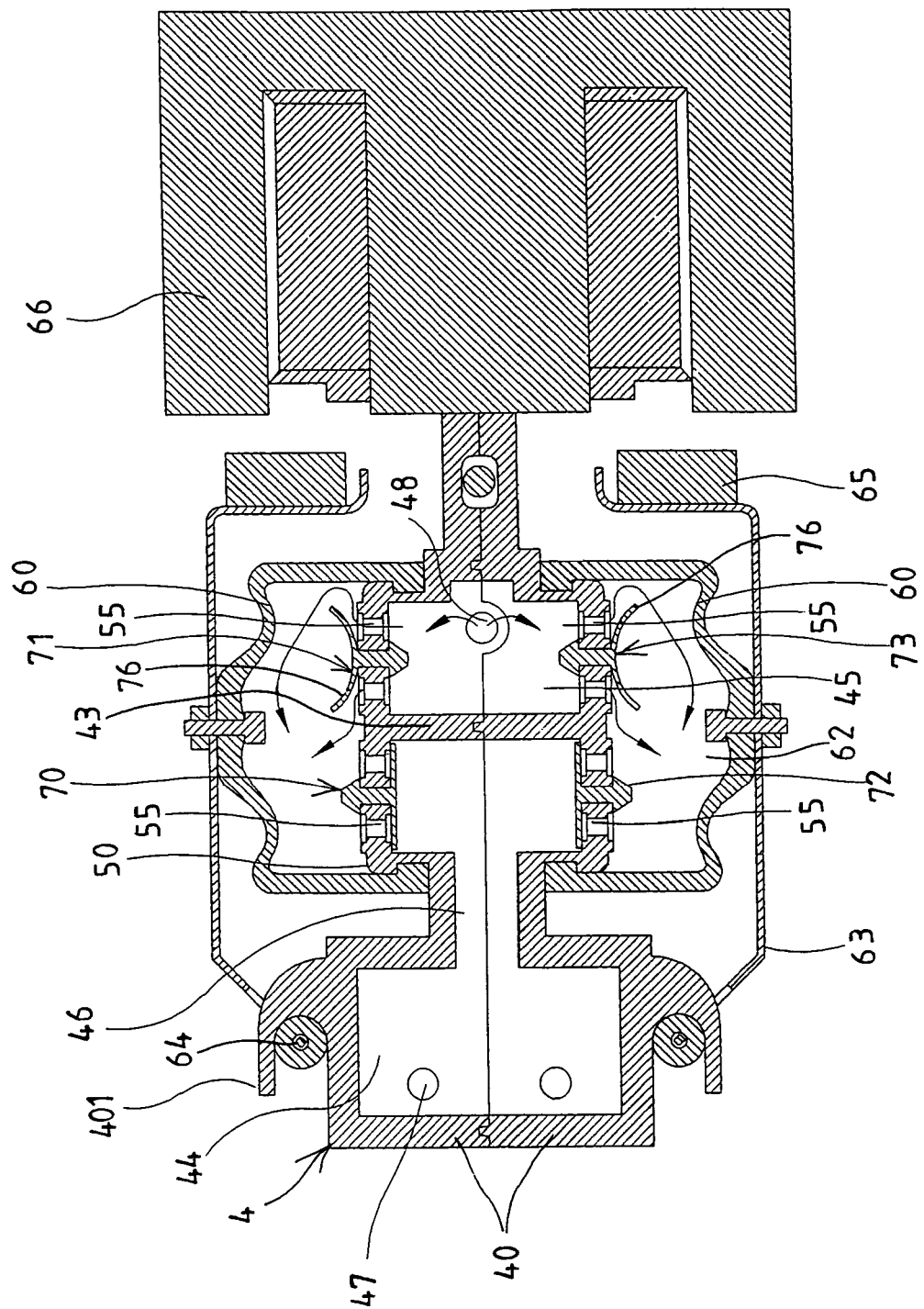
FIG. 5 is a partial cross sectional view of the snivel removing device, taken along lines 5-5 of FIG. 1.
Figure 6:
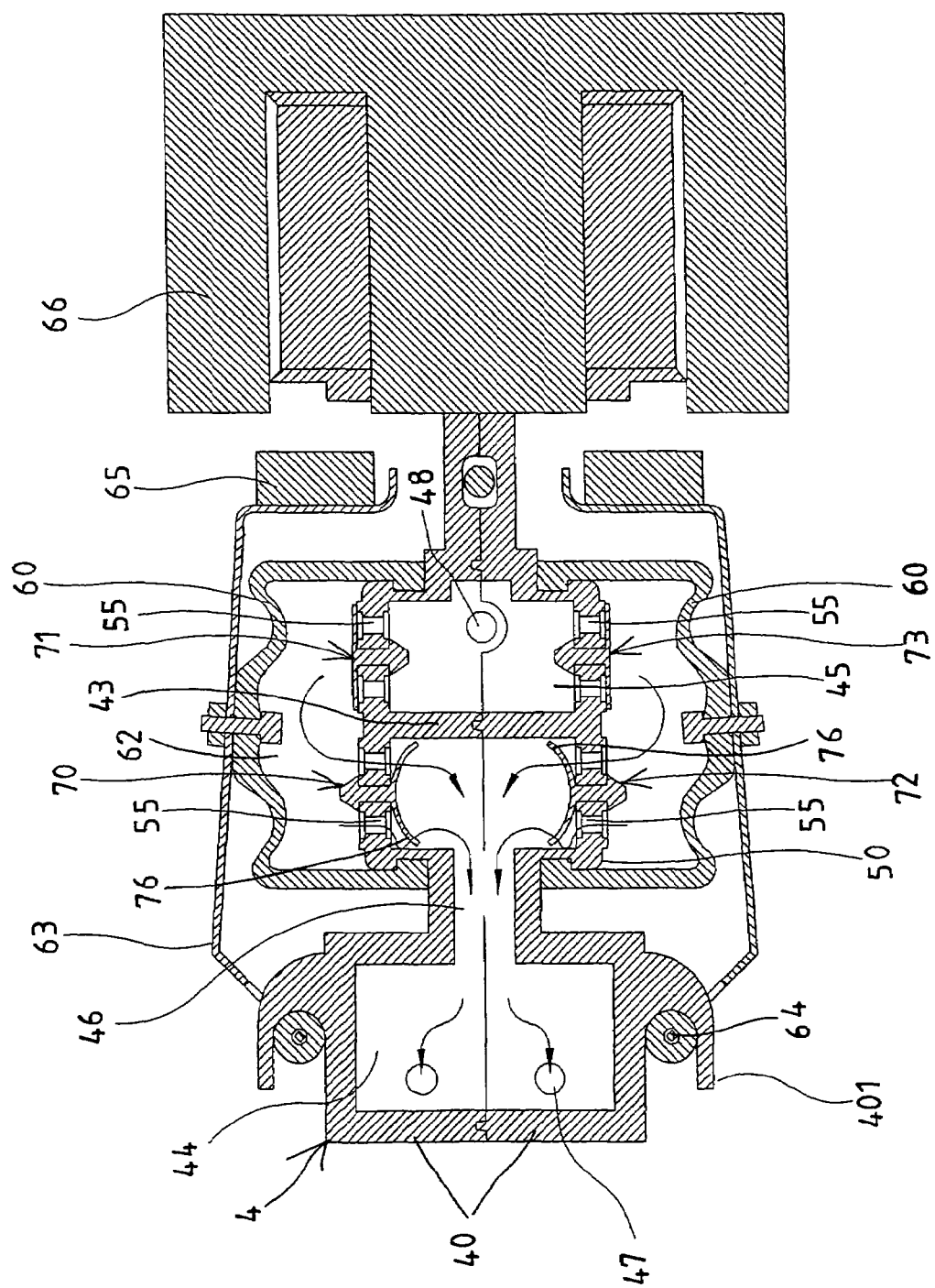
FIG. 6 is a partial cross sectional view similar to FIG. 5, illustrating the operation of the snivel removing device.

The housing 4 includes a partition 43 provided therein, such as extended from the housing members 40, to separate the inner portion of the housing 4 into two chambers 44, 45, as shown in FIGS. 3-6, and preferably includes a narrowed neck portion 46 formed in a middle portion of the chamber 44 thereof (FIGS. 5, 6). The housing 4 further includes one or more, such as two tubes or outlet ports 47 provided thereon, or extended therefrom, such as extended from the two housing members 40 respectively, and communicating with the chamber 44 thereof, and aligned with or engaged with the pathways 27 of the platform 20 respectively.

The housing 4 further includes an inlet tube or inlet port 48 provided thereon, or extended therefrom, such as extended from one of the housing members 40, and communicating with the other chamber 45 thereof, and aligned with or engaged with the passage 25 of the platform 20, for engaging with a hose 90 (FIG. 2). For example, the hose 90 may be engaged through the passage 25 of the platform 20 and attached or coupled to the inlet port 48 of the housing 4, for allowing the snivel or water or cleaning detergents to flow into the chamber 45 of the housing 4. One of the housing members 40 includes a recess 49 formed therein (FIGS. 3, 4), to receive the inlet port 48 therein.

The housing 4 further includes two casings 50 oppositely protruded from the housing members 40 thereof, and having the partition 43 extended from the middle portions of the casings 50 respectively, to have the casings 50 communicated with the chambers 44, 45 of the housing 4, and further includes two holes 51, 52; 53, 54 formed in each of the casings 50, and located in different side of partition 43, and communicating with the chambers 44, 45 of the housing 4 respectively, and further includes a number of cavities 55 formed in each of the casings 50 and arranged around the holes 51, 52; 53, 54 of the casings 50 respectively, and also communicating with the chambers 44, 45 of the housing 4 respectively.

It is preferable that the housing 4 further includes two annular depressions 56 formed in each of the casings 50 and arranged around the holes 51, 52; 53, 54 of the casings 50 respectively, and communicating with the cavities 55 of the housing 4 respectively, to form or define two peripheral bulges 57, 58, in which the inner peripheral bulge 57 is formed and located around the holes 51, 52; 53, 54 of the casings 50 respectively, and the outer peripheral bulge 58 is formed and located around the cavities 55 of the housing 4 respectively, or to have the cavities 55 of the housing 4 formed and located between the two peripheral bulges 57, 58.

One or more, such as two bladders 60 are attached onto the casings 50 respectively, and each includes a chamber 62 formed therein (FIGS. 3, 5-6), and arranged or located between the bladders 60 and the casings 50 respectively, and the bladders 60 are deformable or compressible and expandable to force air or water or snivel or cleaner detergents through the cavities 55 of the housing 4 (FIGS. 5, 6), which will be discussed hereinafter. Two arms 63 are further provided and attached or coupled to the bladders 60 respectively, for depressing or compressing and expanding the bladders 60 respectively.

For example, the housing 4 further includes two hooks or retainers 401 provided thereon, such as extended from the housing members 40 respectively, and located close to the outlet ports 47. The arms 63 each includes a middle portion attached or coupled to the bladders 60 respectively, and one end 64 hooked or pivotally coupled to the housing 4 with the retainers 401, and the other end or the free end having a magnet or magnetic member 65 attached thereto.

An electro-magnetic device 66 is attached to the housing 4, and disposed close to or beside the magnetic members 65 of the arms 63, for generating electro-magnetic field or force to force or to move the magnetic member 65 toward each other, and/or away from each other, in order to actuate the arms 63 to depress or compress and expand the bladders 60 respectively, and thus to force the air or water or snivel or cleaner detergents to flow between the chambers 62 of the bladders 60 and the chambers 44, 45, of the housing 4 and/or of the casings 50. It is preferable that the electro-magnetic device 66 is disposed or supported in the compartment 24 of the platform 20, and the fence 22 may prevent the water or the snivel to flow into the compartment 24 of the platform 20, and thus to prevent the electro-magnetic device 66 from being wetted and damaged.

Four check valves 70, 71, 72, 73 each includes a shank 74 extended therefrom, for engaging through the holes 51, 52; 53, 54 of the casings 50 respectively, and each further includes a ratchet catch 75 provided on the shank 74, for engaging through the holes 51, 52; 53, 54 of the casings 50 respectively, and for engaging with the casings 50, for anchoring or securing the check valves 70-73 to the casings 50 and between the bladders 60 and the chambers 44, 45, of the housing 4 and/or of the casings 50 respectively. After the ratchet catch 75 have been engaged through the holes 51-54 and engaged with or anchored to the casings 50, one end or a free end portion of the shank 74 may be cut off (FIGS. 5, 6).

Each of the check valves 70, 71, 72, 73 includes a resilient blade 76 formed or provided on one end of the shank 74, for engaging with the peripheral bulges 57, 58 of the casings 50 respectively, and for selectively blocking or opening the cavities 55 of the housing 4 respectively, best shown in FIGS. 5, 6, in order to form the check valves 70, 71, 72, 73, and so as to control the flowing of the air or water or snivel or cleaner detergents between the chambers 62 of the bladders 60 and the chambers 44, 45, of the housing 4 and/or of the casings 50.

For example, as shown in FIG. 5, when the magnetic member 65 are forced or moved away from each other by the electro-magnetic device 66, the bladders 60 may be expanded by the arms 63, and the check valves 71, 73 are arranged to be opened by the bladders 60, to allow the air or water or snivel or cleaner detergents to flow or to be drawn form the chamber(s) 45 of the housing 4 and/or of the casings 50 toward the chambers 62 of the bladders 60, and thus to allow the air or water or snivel or cleaner detergents to be drawn into the chamber(s) 45 of the housing 4 and/or of the casings 50 via the inlet port 48 of the housing 4.

At this moment, the other check valves 70, 72 are arranged to enclose the chamber(s) 44 of the housing 4 and/or of the casings 50 by the bladders 60, to prevent the air or water or snivel or cleaner detergents from flowing backward form the chamber(s) 44 of the housing 4 and/or of the casings 50 toward the chambers 62 of the bladders 60, and thus to allow the air or water or snivel or cleaner detergents to be drawn from the chamber(s) 45 of the housing 4 and/or of the casings 50 into the chambers 62 of the bladders 60 only.

On the contrary, as shown in FIG. 6, when the magnetic member 65 are forced or moved toward each other by the electro-magnetic device 66, the bladders 60 may be compressed by the arms 63, and the check valves 70, 72 are arranged to be opened by the bladders 60, to allow the air or water or snivel or cleaner detergents to be forced to flow form the chambers 62 of the bladders 60 toward the chamber (s) 44 of the housing 4 and/or of the casings 50, and then to allow the air or water or snivel or cleaner detergents to flow out of the housing 4 via the outlet ports 47 of the housing 4.

At this moment, the other check valves 71, 73 are arranged to be forced to enclose the chamber(s) 45 of the housing 4 and/or of the casings 50 by the depressing or compressing or pumping force of the bladders 60, to prevent the air or water or snivel or cleaner detergents from flowing backward form the chambers 62 of the bladders 60 toward the chamber(s) 45 of the housing 4 and/or of the casings 50, and thus to prevent the air or water or snivel or cleaner detergents from being forced to flow backwardly into the chamber(s) 45 of the housing 4 and/or of the casings 50.

In operation, when the bladders 60 are expanded, the air or water or snivel or cleaner detergents may be drawn to flow into the chamber(s) 45 of the housing 4 and/or of the casings 50 via the inlet port 48 of the housing 4, and then to flow form the chamber(s) 45 of the housing 4 and/or of the casings 50 toward the chambers 62 of the bladders 60. The air or water or snivel or cleaner detergents may then be forced to flow form the chambers 62 of the bladders 60 toward the chamber(s) 44 of the housing 4 and/or of the casings 50, and then to flow out through the outlet ports 47 of the housing 4 when the bladders 60 are depressed or compressed, such that the air or water or snivel or cleaner detergents may be pumped to flow form the inlet port 48 of the housing 4 to the outlet ports 47 of the housing 4 by the bladders 60 step by step.

The arms 63 and the magnetic member 65 and the electro-magnetic device 66 may thus be formed as an actuating means or device for depressing or compressing or pumping the bladders 60, to draw the snivel into one of the chambers 45 of the housing 4 and/or of the casings 50 via the inlet port 48 of the housing 4, and then to force the snivel to flow into the other chamber 44 of the housing 4 and/or of the casings 50, and then to force the snivel to flow out through the outlet port 47 of the housing 4. The magnetic member 65 and the electro-magnetic device 66 may thus be formed as an operating means or device for actuating or operating the arms 63 to depress or compress or pump or to expand the bladders 60, in order to draw and to force the snivel to flow form the inlet port 48 of the housing 4 to the outlet ports 47 of the housing 4.

Referring again to FIGS. 1 and 2, the snivel removing device 10 further includes a container 80 disposed in the outer receptacle 11, and preferably engaged in the front opening 14 of the outer receptacle 11. For example, the container 80 includes a peripheral groove 81 formed therein, for engaging with the outer receptacle 11, and thus for anchoring or positioning the container 80 to the outer receptacle 11, and for preventing the container 80 from being moved relative to the outer receptacle 11. It is preferable that the container 80 is disposed below the platform 20, best shown in FIG. 1.

The container 80 includes a partition 82 disposed therein, to separate the inner portion of the container 80 into two spaces 83, 84, in which the first space 83 is coupled to the hose 90 and thus the inlet port 48 of the housing 4, to supply the air or snivel or water or cleaning detergents into the chamber 45 of the housing 4, and the first space 83 is also coupled to a nozzle 85 via such as a hose 86. The nozzle 85 may be engaged into the nose of the user, to receive the snivel from the user, and may be engaged into a reservoir of water or cleaner detergents, to receive the water or cleaner detergents from the reservoir, for example.

The container 80 further includes one or more, such as two entrances 87 disposed or provided or formed therein, and communicating with the other or the second space 84 thereof, for receiving or engaging with the outlet tubes or outlet ports 47 of the housing 4 respectively, and for receiving the air or snivel or water or cleaning detergents from the chamber 44 of the housing 4. A further hose 88 may further be provided and coupled to the other space 84 of the container 80, for discharging the air or snivel or water or cleaning detergents from the other space 84 of the container 80. The hose 88 may also be coupled to a collecting box (not shown), for collecting the air or snivel or water or cleaning detergents.

In operation, when the nozzle 85 is engaged into the nose of the user or into a reservoir of water or cleaner detergents, and when the electro-magnetic device 66 is actuated or energized, the bladders 60 may be expanded and compressed in reciprocating action, in order to pump or to draw the snivel or the water or cleaner detergents from the user or from the reservoir, into the first space 83 of the container 80, and then into the chamber(s) 45 of the housing 4 and/or of the casings 50, and then into the chambers 62 of the bladders 60, and then into the other chamber(s) 44 of the housing 4 and/or of the casings 50, and then to flow out through the outlet ports 47 of the housing 4, and into the other or the second space 84 of the container 80.

The snivel removing device may thus be used to draw or to suck or to vacuum the snivel from the users. After cleaning or snivel removing operations, the nozzle 85 may be engaged into a water reservoir which includes a water and/or a cleaning detergent disposed therein, for drawing the water and/or the cleaning detergent into the container 80 and the housing 4 and the casings 50 and the bladders 60, in order to wash or to clean the snivel removing device.

Accordingly, the snivel removing device in accordance with the present invention may be actuated or operated by electric actuating device, and may be used for easily vacuuming or drawing and cleaning or removing snivel or nasal mucus from the users or patients.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A snivel removing device comprising:
   a housing including a partition provided therein, to separate an inner portion of said housing into a first chamber and a second chamber, said housing including at least one outlet port provided thereon and communicating with said first chamber thereof, and including an inlet port provided thereon and communicating with said second chamber thereof, for coupling to a nose of a user, to receive the snivel from the user,
   at least one bladder attached to said housing, and communicating with said first chamber and said second chamber of said housing,
   a first check valve attached to said housing and disposed between said at least one bladder and said first chamber of said housing and arranged to allow the snivel to flow from said at least one bladder into said first chamber of said housing only and to prevent the snivel from flowing backward from said first chamber of said housing into said at least one bladder,
   a second check valve attached to said housing and disposed between said at least one bladder and said second chamber of said housing and arranged to allow the snivel to flow from said second chamber of said housing into said at least one bladder only and to prevent the snivel from flowing backward from said at least one bladder into said second chamber of said housing,
   an arm attached to said at least one bladder,
   a magnetic member attached to said arm, and
   an electro-magnetic device to actuate said magnetic member and to operate said arm to depress and to expand said at least one bladder in order to draw the snivel from said inlet port of said housing toward said at least one outlet port of said housing.

2. The snivel removing device as claimed in claim 1, wherein said housing includes a first cavity and a second cavity formed therein and communicating with said first and said second chambers of said housing respectively, said first and said second check valves each includes a shank extended therefrom, for engaging through said housing, and each includes a ratchet catch provided on said shank for engaging with said housing, to anchor and secure said first and said second check valves to said housing, and each includes a blade provided on said shank for engaging with said housing, and for selectively blocking said first and said second cavities of said housing respectively.

3. The snivel removing device as claimed in claim 2, wherein said shanks of said first and said second check valves each includes a free end portion cut off after said ratchet catches have been engaged through and engaged with said housing.

4. The snivel removing device as claimed in claim 2, wherein said housing includes two annular depressions formed therein and communicating with said first and said second cavities of said housing respectively, to form two peripheral bulges which are located around said first and said second cavities of said housing respectively, and provided for engaging with said blades of said first and said second check valves respectively.

5. The snivel removing device as claimed in claim 1, wherein said housing includes a retainer provided thereon, and said arm includes a first end pivotally coupled to said retainer of said housing, and a second end having said magnetic member attached thereto.

6. The snivel removing device as claimed in claim 1 further comprising a container including at least one entrance provided therein, for engaging with said at least one outlet port of said housing, and for receiving the snivel from said first chamber of said housing.

7. The snivel removing device as claimed in claim 6, wherein said container includes a partition disposed therein, to separate an inner portion of said container into a first space and a second space, said first space is coupled to said inlet port of said housing, and said second space is communicating with said at least one entrance of said container, to receive the snivel from said first chamber of said housing.

8. The snivel removing device as claimed in claim 7, wherein said container includes a nozzle coupled to said first space of said container, for engaging into the nose of the user, to receive the snivel from the user.

9. The snivel removing device as claimed in claim 6 further comprising an outer receptacle including an opening formed therein, said container being engaged in said opening of said outer receptacle, and including a peripheral groove formed therein, for engaging with said outer receptacle, and for anchoring said container to said outer receptacle.

10. The snivel removing device as claimed in claim 9 further comprising a platform disposed in said outer receptacle, to support said housing in said outer receptacle.

11. The snivel removing device as claimed in claim 10, wherein said outer receptacle includes a plurality of studs disposed therein and engaged with said platform, to support said platform within said outer receptacle.

12. The snivel removing device as claimed in claim 11, wherein said studs each includes an enlarged head for engaging with said outer receptacle, and a ratchet catch for engaging with said platform, to anchor said platform within said outer receptacle.

13. The snivel removing device as claimed in claim 12, wherein said studs each includes a pin extended from said ratchet catch thereof, for allowing said ratchet catch to be easily engaged through said platform, and said pin is cut off from said stud after said ratchet catch has been engaged through said platform to secure said platform within said outer receptacle.

14. The snivel removing device as claimed in claim 10, wherein said platform includes a pathway formed therein and aligned with said at least one outlet port of said housing, and includes a passage formed therein and aligned with said inlet port of said housing.

15. The snivel removing device as claimed in claim 10, wherein said platform includes a fence extended therein, to separate an inner portion of said platform into two separated compartments.

* * * * *